US011946938B2

(12) United States Patent
Wienhues-Thelen et al.

(10) Patent No.: US 11,946,938 B2
(45) Date of Patent: Apr. 2, 2024

(54) CIRCULATING ANGIOPOIETIN-2 (ANG-2) AND INSULIN-LIKE GROWTH FACTOR-BINDING PROTEIN 7 (IGFBP7) FOR THE PREDICTION OF STROKE (71) Applicant: Roche Diagnostics Operations, Inc., Indianapolis, IN (US)

(72) Inventors: Ursula-Henrike Wienhues-Thelen, Krailling (DE); Johann Karl, Peissenberg (DE); Peter Kastner, Murnau am Staffelsee (DE); Vinzent Rolny, Munich (DE); Andre Ziegler, Laeufelfingen (CH); David Conen, Ancaster (CA)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/899,629

(22) Filed: Jun. 12, 2020

(65) Prior Publication Data
US 2020/0300869 A1 Sep. 24, 2020

Related U.S. Application Data (63) Continuation of application No. PCT/EP2018/084577, filed on Dec. 12, 2018.

(30) Foreign Application Priority Data

Dec. 13, 2017 (EP) ..................................... 17207096

(51) Int. Cl.
G01N 33/53 (2006.01)
G01N 33/68 (2006.01)

(52) U.S. Cl.
CPC . G01N 33/6893 (2013.01); G01N 2333/4745 (2013.01); G01N 2333/515 (2013.01); G01N 2800/326 (2013.01); G01N 2800/50 (2013.01)

(58) Field of Classification Search
None
See application file for complete search history.

(56) References Cited

U.S. PATENT DOCUMENTS

| | | | |
|---|---|---|---|
| 4,016,043 A | 4/1977 | Schuurs et al. | |
| 4,018,653 A | 4/1977 | Mennen | |
| 4,424,279 A | 1/1984 | Bohn et al. | |
| 2003/0119064 A1* | 6/2003 | Valkirs | G01N 33/573 435/7.1 |
| 2007/0027456 A1* | 2/2007 | Gartner | A61B 17/0057 606/113 |
| 2011/0294690 A1 | 12/2011 | Montaner Vilallonga | |
| 2012/0021989 A1* | 1/2012 | Holm | A61P 7/00 435/6.1 |
| 2013/0085079 A1 | 4/2013 | Gill et al. | |
| 2015/0018234 A1 | 1/2015 | Sharp et al. | |
| 2015/0233946 A1* | 8/2015 | Block | G01N 33/6869 435/7.94 |
| 2016/0091499 A1 | 3/2016 | Sterling et al. | |
| 2017/0102396 A1 | 4/2017 | Hess et al. | |

FOREIGN PATENT DOCUMENTS

| | | |
|---|---|---|
| CN | 101041855 A | 9/2007 |
| CN | 102221615 A | 10/2011 |
| JP | 2014528576 A | 10/2014 |
| JP | 2017530356 A | 10/2017 |
| WO | 2008/089994 A1 | 7/2008 |
| WO | 2012/107419 A1 | 8/2012 |
| WO | 2013049674 A1 | 4/2013 |
| WO | 2014/040759 A1 | 3/2014 |
| WO | 2014/072500 A1 | 5/2014 |
| WO | 2015/185672 A2 | 12/2015 |
| WO | 2016048388 A1 | 3/2016 |
| WO | 2016/066698 A1 | 5/2016 |
| WO | 2017/216387 A1 | 12/2017 |

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Christiansen et al., Atrial fibrillation and risk of stroke: a nationwide cohort study, Europace, Feb. 2016, 18, pp. 1689-1697. (Year: 2016).*
Bontekoe et al., Abstract 18466: Angiopoietin-2 as a predictive biomaker of atrial fibrillation in patients with stage 5 chronic kidney disease, Circulation vol. 136,Suppl 1, Nov. 14, 2017, p. A18466). (Year: 2017).*
Patel et al., Angiopoietin-2 levels as a biomarker of cardiovascular risk in patients with hypertension, Annuals of Medicine, 2008, 40, pp. 215-222). (Year: 2008).*
Kin et al., Development of a novel automated ELISA analyzer based on an electrochemical detector, Proceedings of the 32nd ISR (International Symposium on Robotics), Apr. 2001, pp. 439-443.. (Year: 2001).*
Blum, Steffen et al., Prospective Assessment of Sex-Related Differences in Symptom Status and Health Perception Among Patients With Atrial Fibrillation, Journal of the American Heart Association, 2017, e005401, 7 pp., vol. 6.

(Continued)

Primary Examiner — Gary Counts
(74) Attorney, Agent, or Firm — Stinson LLP (57) ABSTRACT The present disclosure demonstrates a method for predicting the risk of stroke of a subject and a method for improving the prediction accuracy of a clinical stroke risk score. The methods are based on the determination of the amount of Angiopoietin-2 (Ang-2) and/or the amount of Insulin-like growth factor-binding protein 7 (IGFBP7) in a sample from a subject. Moreover, disclose is the use of i) the biomarker Ang-2 and/or the biomarker IGFBP7, and/or ii) at least one detection agent that specifically binds to Ang-2 and/or at least one detection agent that specifically binds to IGFBP7 in a sample from a subject for predicting the risk of stroke of said subject.

11 Claims, 2 Drawing Sheets (56) References Cited

OTHER PUBLICATIONS

Cheung, Anthony H. et al., Endothelial Tie2/Tek Ligands Angiopoietin-1 (ANGPT1) and Angiopoietin-2 (ANGPT2): Regional Localization of the Human Genes to 8q22.3-q23 and 8p23, Genomics, 1998, pp. 389-391, vol. 48, Issue 3.
Choudhury, Anirban et al., Relationship of Soluble CD40 Ligand to Vascular Endothelial Growth Factor, Angiopoietins, and Tissue Factor in Atrial Fibrillation A Link Among Platelet Activation, Angiogenesis, and Thrombosis?, Chest, 2007, pp. 1913-1919, vol. 132, No. 6.
Chugh, Sumeet S. et al., Worldwide Epidemiology of Atrial Fibrillation A Global Burden of Disease 2010 Study, Circulation, 2014, pp. 837-847, vol. 129.
Conen, David, Entzündung, oxidativer Stress und Fibrose bei der Entwicklung und Progression von Vorhofflimmern, Forum Med Suisse, 2012, pp. 860 862, vol. 12, No. 44, English portions only.
Freestone, Bethan et al., Angioegenic factors in atrial fibrillation: A possible role in thrombogenesis?, Annals of Medicine, 2005, pp. 365-372, vol. 37.
Fuster, Valentin et al., ACC/AHA/ESC 2006 Guidelines for the Management of Patients With Atrial Fibrillation, Circulation, 2006, pp. e257-e354, vol. 114, No. 7.
Gage, Brian F. et al., Validation of Clinical Classification Schemes for Predicting Stroke Results from the National Registry of Atrial Fibrillation, JAMA, 2001, pp. 2864-2870, vol. 285, No. 2.
Gandhi, Parul U. et al., Prognostic Usefulness of Insulin-Like Growth Factor-Binding Protein 7 in Heart Failure With Reduced Ejection Fraction: A Novel Biomarker of Myocardial Diastolic Function?, American Journal of Cardiology, 2014, pp. 1543-1549, vol. 114.
Gandhi, Parul U. et al., Prognostic Value of Insulin-Like Growth Factor-Binding Protein 7 in Patients with Heart Failure and Preserved Ejection Fraction, Journal of Cardiac Failure, 2017, pp. 20-28, vol. 23, No. 1.
Go, Alan S. et al., Prevalence of Diagnosed Atrial Fibrillation in Adults, JAMA, 2001, pp. 2370-2375, vol. 285.
Hart, Robert G. et al., Meta-analysis: Antithrombotic Therapy to Prevent Stroke in Patients Who Have Nonvalvular Atrial Fibrillation, Annals of Internal Medicine, 2007, pp. 857-867, vol. 146.
Hijazi, Ziad et al., The ABC (age, biomarkers, clinical history) stroke risk score: a biomarker-based risk score for predicting stroke in atrial fibrillation, European Heart Journal, 2016, 9 pp.
Hijazi, Ziad et al., The novel biomarker-based ABC (age, biomarkers, clinical history)-bleeding risk score for patients with atrial fibrillation: a derivation and validation study, The Lancet, 2016, 2302-2311, vol. 387.
International Search Report dated Jan. 18, 2019, in Application No. PCT/EP2018/084577, 4 pages.
Kirchhof, Paulus et al., 2016 ESC Guidelines for the management of atrial fibrillation developed in collaboration with EACTS, European Heart Journal, 2016, pp. 2893-2962, vol. 37.
Lukasz, Alexander et al., Angiopoietin-2 in Adults with Congenital Heart Disease and Heart Failure, PLoS, 2013, e66861, 8 pp., vol. 8, No. 6.
Maisonpierre, Peter C. et al., Angiopoietin-2, a Natural Antagonist for Tie2 That Disrupts in vivo Angiogenesis, Science, 1997, pp. 55-60, vol. 277.
Oldgren, Jonas et al., Performance and Validation of a Novel Biomarker-Based Stroke Risk Score for Atrial Fibrillation, Circulation, 2016, pp. 1697-1707, vol. 134.
Ono, Yasuhiro et al., Expression of prostacyclin-stimulating factor, a novel protein, in tissues of Wistar rats and in cultured cells, Biochemical and Biophysical Research Communications, 1994, pp. 1490-1496, vol. 202, No. 3.
Pöss, Janine et al., Angiopoietin-2 and outcome in patients with acute decompensated heart failure, Clinical Research in Cardiology, 2015, pp. 380-387, vol. 104.
Richter, Mark M., Electrochemiluminescence (ECL), Chemical Reviews, 2004, pp. 3003-3036, vol. 104.
Wong, Adrianne L. et al., Tie2 Expression and Phosphorylation in Angiogenic and Quiescent Adult Tissues, Circulation Research, 1997, pp. 567-574, vol. 81.
Yancopoulos, George D. et al., Vascular-specific growth factors and blood vessel formation, Nature, 2000, pp. 242-248, vol. 407.
Zweig, Mark H. and Campbell, Gregory, Receiver-Operating Characteristic (ROC) Plots: A Fundamental Evaluation Tool in Clinical Medicine, Clinical Chemistry, 1993, pp. 561-577, vol. 39, No. 4.
Kitagawa, Embolic Stroke of Undetermined Sources (ESUS); 2016, vol. 33, pp. 382-386. English Abstract, English portions only.
M. Son et al., Risk of Ischemic Stroke After Atrial Fibrillation Diagnosis: A National Sample Cohort, PLoS ONE 12 (6): e0179687, Jun. 21, 2017, pp. 1-13.

* cited by examiner

CIRCULATING ANGIOPOIETIN-2 (ANG-2) AND INSULIN-LIKE GROWTH FACTOR-BINDING PROTEIN 7 (IGFBP7) FOR THE PREDICTION OF STROKE

CROSS-REFERENCE TO RELATED APPLICATIONS

This application is a continuation of International Application No. PCT/EP2018/084577 filed Dec. 12, 2018, which claims priority to European Application No. 17207096.3 filed Dec. 13, 2017, the disclosures of which are hereby incorporated by reference in their entirety.

BACKGROUND

The present invention relates to a method for predicting the risk of stroke of a subject and to a method for improving the prediction accuracy of a clinical stroke risk score. The methods of the present invention are based on the determination of the amount of Angiopoietin-2 (Ang-2) and/or the amount of Insulin-like growth factor-binding protein 7 (IGFBP7) in a sample from a subject. Moreover, the present invention pertains to the use of i) the biomarker Ang-2 and/or the biomarker IGFBP7, and/or ii) at least one detection agent that specifically binds to Ang-2 and/or at least one detection agent that specifically binds to IGFBP7 in a sample from a subject for predicting the risk of stroke of said subject.

Stroke ranks after ischemic heart disease second as a cause of lost disability—adjusted—life years in high-income countries and as a cause of death worldwide. In order to reduce the risk of stroke, anticoagulation therapy appears the most appropriate therapy.

Atrial fibrillation (AF) is an important risk factor for stroke (Hart et al., Ann Intern Med 2007; 146(12): 857-67; Go A S et al. JAMA 2001; 285(18): 2370-5). Atrial fibrillation is characterized by irregular heart beating and often starts with brief periods of abnormal beating that can increase over time and may become a permanent condition. An estimated 2.7-6.1 million people in the United States have atrial fibrillation and approximately 33 million people globally (Chugh S. S. et al., Circulation 2014; 129:837-47).

It is important to assess which patients with AF have the highest risk of atrial fibrillation and thus may benefit from an intensified anticoagulation therapy to reduce the risk of stroke (Hijazi et al., European Heart Journal doi:10.1093/eurheartj/ehw054. 2016).

The CHADS2, the CHA2DS2-VASc score, and the ABC score are clinical prediction rules for estimating the risk of stroke in patients with atrial fibrillation. The scores are used to assess whether or not treatment is required with anticoagulation therapy. The ABC-stroke score includes age, biomarkers (N-terminal fragment B-type natriuretic peptide and high-sensitivity cardiac troponin), and clinical history (prior stroke), see Oldgren et al., Circulation. 2016; 134:1697-1707).

Angiopoietins are glycoproteins that are involved in angiogenesis. Because they are also expressed in healthy tissue, they are supposed to stabilize existing vessels and modulating the interaction between endothelial cells and surrounding vascular smooth muscle cells (Wong A L, et al. Circ Res. 1997; 81:567-74). Four angiopoietins are known, angiopoietin-1 (Ang-1) to angiopoietin-4 (Ang-4). Human angiopoietin-2 (Ang-2) is e.g. described in Maisonpierre P C et al. (Science 277 (1997) 55-60 and Cheung, A. H., et al, Genomics 48 (1998) 389-91) and is one of four members of the angiopoietin family. Ang-2 was discovered as ligand for the Ties, a family of tyrosine kinases that is selectively expressed within the vascular endothelium (Yancopoulos, G. D., et al., Nature 407 (2000) 242-48).

While Ang-1 is an agonist of the endothelial cell-specific Tie2 receptor tyrosine kinase and has pro-angiogenetic properties, it was found that Ang-2 disrupts blood vessel formation and has antagonistic signaling action through the Tie-2 receptor (Maisonpierre P C et al., Science 1997; 277:55-60)

Angiopoietin-2 (Ang-2) is known to impair endothelial integrity and has been shown elevated in heart failure (see e.g. Poss et al. Angiopoietin-2 and outcome in patients with acute decompensated heart failure. Clin Res Cardiol. May 2015; 104(5):380-387 or, or Lukasz et al. Angiopoietin-2 in adults with congenital heart disease and heart failure. PLoS One. 2013; 8(6):e66861).

Ang-2 has been found to be elevated in patients with atrial fibrillation (Freestone et al., Angiogenic factors in atrial fibrillation: a possible role in thrombogenesis? Ann Med 2005; 37: 365-72 or Choudhury et al., Relationship of Soluble CD40 Ligand to Vascular Endothelial Growth Factor, Angiopoietins, and Tissue Factor in atrial fibrillation, CHEST 2007; 132:1913-1919).

The international patent application PCT/EP2017/064970 discloses that Ang-2 and IGFB7 can be used for the prediction of recurrence of atrial fibrillation.

WO 2014/072500 discloses IGPBP7 as a biomarker for the diagnosis of atrial fibrillation.

WO 2014/040759 discloses IGFBP7 as a predictor of cardiovascular events and mortality. Further, IGFBP-7 has been found to be elevated in patients with heart failure with reduced ejection at risk of cardiovascular events (Ghandi et al., Am J Cardiol 2014; 114:1543e1549). IGFBP-7 levels were found to be prognostic in patients with HFpEF with regard to all-cause mortality, cardiovascular hospitalization, and a composite of HF hospitalization or HF death (Ghandi et al. J Cardiac Failure 2017). The primary outcome was a composite of all-cause mortality and protocol-specified cardiovascular hospitalization, which was defined as hospitalization for worsening HF, myocardial infarction, stroke, unstable angina, ventricular or atrial dysrhythmia, or myocardial infarction or stroke that occurred with any hospitalization. However, no data are shown for IGFBP-7 levels in association with the outcome stroke.

The prediction of stroke and the selection of preventive medication are important clinical unmet needs.

Up to now, IGFBP7 and Ang-2 have not been used to predict the stroke in patients having already atrial fibrillation.

The technical problem underlying the present invention can be seen as the provision of methods for complying with the aforementioned needs. The technical problem is solved by the embodiments characterized in the claims and herein below.

Advantageously, it was found in the context of the studies of the present invention that the determination of the amount of Ang-2 and/or IGFBP7 in a sample from a subject allows for stroke prediction.

BRIEF SUMMARY OF THE INVENTION

The present method for predicting the risk of stroke of a subject, comprising the steps of
(a) determining the amount of Angiopoietin-2 (Ang-2) and/or the amount of Insulin-like growth factor-binding protein 7 (IGFBP7) in a sample from the subject, and (b) comparing the amount of Ang-2 and/or the amount of IGFBP7 to a reference amount, whereby the risk of stroke is predicted.

In an embodiment of the method of the present invention, the subject suffers from atrial fibrillation.

In an embodiment of the method of the present invention, the atrial fibrillation is paroxysmal, persistent or permanent atrial fibrillation.

In an embodiment of the method of the present invention, the subject has a history of stroke or TIA (transient ischemic attack)

In an embodiment of the method of the present invention, the age of the subject is 65 years of age or older. Further, the age of the subject may be 55 years or older.

In an embodiment of the method of the present invention, the subject receives anticoagulation therapy.

In an embodiment of the method of the present invention, stroke is cardioembolic stroke.

In an embodiment of the method of the present invention, the subject is human.

In an embodiment of the method of the present invention, wherein the sample is blood, serum or plasma.

In an embodiment of the method of the present invention, an amount of Ang-2 and/or an amount of IGFBP7 which is increased as compared to the reference amount is indicative for a subject who is at risk to suffer from stroke and/or an amount of Ang-2 and/or an amount of IGFBP7 which is decreased or not altered as compared to the reference amount is indicative for a subject who is at not at risk to suffer from stroke.

In an embodiment of the method of the present invention, the predictive window is a period of up to 10 years.

In an embodiment of the method of the present invention, the predictive window is a period of about 5 years.

In a particular preferred embodiment of the method of the present invention, the predictive window is a period of up to 3 years.

In an embodiment of the method of the present invention, the method further comprising the step of recommending anticoagulation therapy or of recommending an intensification of anticoagulation therapy if the subject has been identified to be at risk to suffer from stroke.

The present invention further concerns a method for predicting the risk of stroke in a subject, comprising the steps of
a) determining the amount of Ang-2 and/or the amount of Insulin-like growth factor-binding protein 7 (IGFBP7) in a sample from the subject having a known clinical stroke risk score,
b) assessing the clinical stroke risk score for said subject, and
c) predicting the risk of stroke based on the results of steps a) and b).

The present invention further relates to a method for improving the prediction accuracy of a clinical stroke risk score for a subject, comprising the steps of
a) determining the amount of Ang-2 and/or the amount of Insulin-like growth factor-binding protein 7 (IGFBP7) in a sample from the subject having a known clinical stroke risk score, and
b) combining a value for the amount of Ang-2 and/or IGFBP-7 with the clinical stroke risk score, whereby the prediction accuracy of said clinical stroke risk score is improved.

In embodiment of the aforementioned method, the method further comprises the assessment of the clinical risk score for said subject.

In an embodiment of the present invention, the clinical stroke risk score is the $CHA_2DS_2$-VASc-Score, the $CHADS_2$-Score or the ABC-Score.

The present invention further relates to the use of
i) the biomarker Ang-2 and/or the biomarker IGFBP7, and/or
ii) at least one detection agent that specifically binds to Ang-2 and/or at least one detection agent that specifically binds to IGFBP7 in a sample from a subject for predicting the risk of stroke of said subject.

The present invention further relates to the use of
i) the biomarker Ang-2 and/or the biomarker IGFBP7, and/or
ii) at least one detection agent that specifically binds to Ang-2 and/or at least one detection agent that specifically binds to IGFBP7 in a sample from a subject for improving the prediction accuracy of a clinical stroke risk score.

The present invention further relates to the use of
i) the biomarker Ang-2 and/or the biomarker IGFBP7, and/or
ii) at least one detection agent that specifically binds to Ang-2 and/or at least one detection agent that specifically binds to IGFBP7,
in a sample from a subject,
in combination with a clinical stroke risk score,
for predicting the risk of a subject to suffer from stroke.

In an embodiment, the detection agent that specifically binds IGFBP7 is an antibody or antigen binding fragment thereof that specifically binds IGFBP7.

In an embodiment, the detection agent that specifically binds Ang-2 is an antibody or antigen binding fragment thereof that specifically binds Ang-2.

BRIEF DESCRIPTION OF THE FIGURES

The FIG. shows the weighted Kaplan-Meier curves for the two patient groups with baseline IGFBP-7 measurement <=178 pg/mL vs >178 pg/mL. As easily seen the risk for the two groups for the occurrence of a stroke differs significantly. As shown in FIG. 1A, IGFBP-7 may help to identify patients at elevated risk of stroke, even in a population of patients with atrial fibrillation that receive oral anticoagulation or vitamin antagonists.

The figures shows the weighted Kaplan-Meier curves for the two patient groups with baseline Angiopoetin-2 measurement <=2.4 ng/ml vs >2.4 ng/ml. As easily seen the risk for the two groups for the occurrence of a stroke differs significantly. As shown in FIG. 1B Ang-2 may help to identify patients at elevated risk of stroke, even in a population of patients with atrial fibrillation that receive oral anticoagulation or vitamin antagonists.

DETAILED DESCRIPTION

Definitions

As set forth above, the present invention relates to a method for predicting the risk of stroke of a subject, comprising the steps of (a) determining the amount of Angiopoietin-2 (Ang-2) and/or the amount of Insulin-like growth factor-binding protein 7 (IGFBP7) in a sample from the subject, and (b) comparing the amount of Ang-2 and/or the amount of IGFBP7 to a reference amount, whereby the risk of stroke is predicted.

The prediction of stroke shall be based on the results of the comparison step (b).

Accordingly, the method of the present invention preferably comprises the steps of (a) determining the amount of Angiopoietin-2 (Ang-2) and/or the amount of Insulin-like growth factor-binding protein 7 (IGFBP7) in a sample from the subject, (b) comparing the amount of Ang-2 and/or IGFBP7 to a reference amount, whereby the risk of stroke is predicted, and (c) predicting the risk of stroke of a subject, preferably based on the results of the comparison step (b)

The method as referred to in accordance with the present invention includes a method which essentially consists of the aforementioned steps or a method which includes further steps. Moreover, the method of the present invention, preferably, is an ex vivo and more preferably an in vitro method. Moreover, it may comprise steps in addition to those explicitly mentioned above. For example, further steps may relate to the determination of further markers and/or to sample pre-treatments or evaluation of the results obtained by the method. The method may be carried out manually or assisted by automation. Preferably, step (a), (b) and/or (c) may in total or in part be assisted by automation, e.g., by a suitable robotic and sensory equipment for the determination in step (a) or a computer-implemented calculation in step (b).

As will be understood by those skilled in the art, the prediction made in connection with present invention is usually not intended to be correct for 100% of the subjects to be tested. The term, preferably, requires that a correct assessment (such as the diagnosis, differentiation, prediction, identification or assessment of a therapy as referred to herein) can be made for a statistically significant portion of subjects. Whether a portion is statistically significant can be determined without further ado by the person skilled in the art using various well-known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98%, or at least 99%. The p-values are, preferably, 0.4, 0.1, 0.05, 0.01, 0.005, or 0.0001.

In accordance with the method of the present invention, the risk of stroke shall be predicted. The term "stroke" is well known in the art. The term, preferably, refers to ischemic stroke, in particular to cerebral ischemic stroke. A stroke which is predicted by the method of the present invention shall be caused by reduced blood flow to the brain or parts thereof which leads to an undersupply of oxygen to brain cells. In particular, the stroke leads to irreversible tissue damage due to brain cell death. Symptoms of stroke are well known in the art. Ischemic stroke may be caused by atherothrombosis or embolism of a major cerebral artery, by coagulation disorders or nonatheromatous vascular disease, or by cardiac ischemia which leads to a reduced overall blood flow. The ischemic stroke is preferably selected from the group consisting of atherothrombotic stroke, cardioembolic stroke and lacunar stroke. Preferably, the stroke to be predicted is an acute ischemic stroke, in particular cardioembolic stroke. A cardioembolic stroke (frequently also referred to as embolic or thromboembolic stroke) can be caused by atrial fibrillation The term "stroke" does, preferably, not include hemorrhagic stroke. Whether a subject suffers from stroke, in particular from ischemic stroke can be determined by well-known methods. Moreover, symptoms of stroke are well known in the art. E.g., stroke symptoms include sudden numbness or weakness of face, arm or leg, especially on one side of the body, sudden confusion, trouble speaking or understanding, sudden trouble seeing in one or both eyes, and sudden trouble walking, dizziness, loss of balance or coordination.

It is known in the art that biomarkers could be increased in various diseases and disorders. This does also apply to Ang-2 and IGFBP7. E.g., IGFBP7 is known to be increased in patients with heart failure. However, this is taken into account by the skilled person. Accordingly, the expression "prediction of the risk of stroke" as an aid in the prediction of a risk of an adverse event associated with atrial fibrillation.

The "subject" as referred to herein is, preferably, a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Preferably, the subject is a human subject.

Preferably, the subject to be tested is of any age, more preferably, the subject to be tested is 50 years of age or older, more preferably 60 years of age or older, and most preferably 65 years of age or older. Further, it is envisaged that the subject to be tested is 70 years of age or older. Moreover, it is envisaged that the subject to be tested is 75 years of age or older. Also, the subject may be between 50 and 90 years. Further, the age of the subject may be 55 years or older.

In a preferred embodiment of the method of the present invention, the subject to be tested suffers from atrial fibrillation. Atrial fibrillation may be paroxysmal, persistent or permanent atrial fibrillation. Thus, the subject may suffer from paroxysmal, persistent or permanent atrial fibrillation. In particular, it is envisaged that the subject suffers from paroxysmal, persistent or permanent atrial fibrillation. It has been shown in the studies underlying the present invention that the determination of the biomarkers as referred to herein allows for a prediction of stroke in all subgroups. The best performance was observed in patients with persistent and permanent atrial fibrillation.

Thus, in an embodiment of the present invention, the subject suffers from paroxysmal atrial fibrillation.

In another embodiment of the present invention, the subject suffers from persistent atrial fibrillation.

In another embodiment of the present invention, the subject suffers from permanent atrial fibrillation.

The term "Atrial Fibrillation" is well known in the art. As used herein, the term preferably refers to a supraventricular tachyarrhythmia characterized by uncoordinated atrial activation with consequent deterioration of atrial mechanical function. In particular, the term refers to an abnormal heart rhythm characterized by rapid and irregular beating. It involves the two upper chambers of the heart. In a normal heart rhythm, the impulse generated by the sino-atrial node spreads through the heart and causes contraction of the heart muscle and pumping of blood. In atrial fibrillation, the regular electrical impulses of the sino-atrial node are replaced by disorganized, rapid electrical impulses which result in irregular heart beats. Symptoms of atrial fibrillation are heart palpitations, fainting, shortness of breath, or chest pain. However, most episodes have no symptoms. On the electrocardiogram atrial fibrillation is characterized by the replacement of consistent P waves by rapid oscillations or fibrillatory waves that vary in amplitude, shape, and timing, associated with an irregular, frequently rapid ventricular response when atrioventricular conduction is intact.

The American College of Cardiology (ACC), American Heart Association (AHA), and the European Society of Cardiology (ESC) propose the following classification system (see Fuster (2006) Circulation 114 (7): e257-354 which herewith is incorporated by reference in its entirety, see e.g. FIG. 3 in the document): First detected AF, paroxysmal AF, persistent AF, and permanent AF.

All people with AF are initially in the category called first detected AF. However, the subject may or may not have had previous undetected episodes. A subject suffers from permanent AF, if the AF has persisted for more than one year. In particular, conversion back to sinus rhythm does not occur (or only with medical intervention). A subject suffers from persistent AF, if the AF lasts more than 7 days. The subject may require either pharmacologic or electrical intervention to terminate atrial fibrillation. Thus persistent AF occurs in episodes, but the arrhythmia does typically not convert back to sinus rhythm spontaneously (i.e. without medical invention). Paroxysmal atrial fibrillation, preferably, refers to an intermittent episode of atrial fibrillation which lasts not longer than 7 days and terminates spontaneously (i.e. without medical intervention). In most cases of paroxysmal AF, the episodes last less than 24 hours. Thus, whereas paroxysmal atrial fibrillation terminates spontaneously, persistent atrial fibrillation does not end spontaneously and requires electrical or pharmacological cardioversion for termination, or other procedures, such as ablation procedures (Fuster (2006) Circulation 114 (7): e257-354). The term "paroxysmal atrial fibrillation" is defined as episodes of AF that terminate spontaneously in less than 48 hours, more preferably in less than 24 hours, and, most preferably in less than 12 hours. Both persistent and paroxysmal AF may be recurrent.

As set forth above, the subject to be tested preferably suffers from paroxysmal, persistent or permanent atrial fibrillation.

Further, it is envisaged that the subject suffers from an episode of atrial fibrillation at the time when the sample is obtained. This may be e.g. the case if the subject suffers from permanent or persistent AF.

Alternatively, it is envisaged that the subject does not suffer from an episode of atrial fibrillation at the time when the sample is obtained. This may be e.g. the case if the subject suffers from paroxysmal AF. Accordingly, the subject shall have a normal sinus rhythm when the sample is obtained, i.e. is in sinus rhythm.

Further, it is contemplated that the atrial fibrillation has been diagnosed previously in the subject. Accordingly, the atrial fibrillation shall be a diagnosed, i.e. a detected, atrial fibrillation.

As shown in the Examples, a prediction of the risk is possible in patients with heart failure. Accordingly, the subject to be tested may suffer from heart failure. The term "heart failure" in accordance with the method of the present invention preferably relates to heart failure with reduced left ventricular ejection fraction.

Further, it has been shown that a prediction of the risk is possible in subjects who do not have a history of heart failure. Accordingly, the subject to be tested preferably does not suffer from heart failure. In particular, the subject to be tested does not suffer from heart failure according to NYHA class II, III, and IV.

In an embodiment of the present invention, the subject does not suffer from heart failure with preserved left ventricular ejection fraction.

In a particular preferred embodiment, the subject is a subject who does not suffer from heart failure, but suffers from atrial fibrillation.

Advantageously, it has been shown in the studies underlying the method of the present invention that a reliable prediction is possible even if the subject already receives anticoagulation therapy, i.e. a therapy which aims to reduce the risk of stroke (about 70% of patients received received oral anticoagulation and about 30% vitamin K antagonists such as warfarin and dicumarol). Surprisingly, it has been shown that by determining the amounts of IGFBP7 and/or Ang-2 it could be differentiated within a population or risk patient, i.e. patients with atrial fibrillation receiving anticoagulation therapy, it could be reliably differentiated between a reduced risk and an increased risk of stroke. AF patients with an increased risk of stroke might benefit from an intensification of anticoagulation therapy. Moreover, AF patients which a reduced risk of stroke might be overtreated and might benefit from a less intense anticoagulation therapy (resulting, e.g., in decreased health care costs).

Thus, it is preferred in accordance with the present invention that the subject receives anticoagulation therapy.

As set forth above, anticoagulation therapy is preferably a therapy which aims to reduce the risk of anticoagulation in said subject. More preferably, anticoagulation therapy is the administration of at least one anticoagulant. Administration of at least one anticoagulant shall aim to reduce or prevent coagulation of blood and related stroke. In a preferred embodiment, at least one anticoagulant is selected from the group consisting of heparin, a coumarin derivative (i.e. a vitamin K antagonist), in particular warfarin or dicumarol, oral anticoagulants, in particular dabigatran, rivaroxaban or apixaban, tissue factor pathway inhibitor (TFPI), antithrombin III, factor IXa inhibitors, factor Xa inhibitors, inhibitors of factors Va and VIIa and thrombin inhibitors (anti-IIa type). Accordingly, it is envisaged that the subject takes at least one of the aforementioned medicaments.

In preferred embodiment, the anticoagulant is a vitamin K antagonist such as warfarin or dicumarol. Vitamin K antagonists, such as warfarin or dicumarol are less expensive, but need better patient compliance, because of the inconvenient, cumbersome and often unreliable treatment with fluctuating time in therapeutic range. NOAC (new oral anticoagulants) comprise direct factor Xa inhibitors (apixaban, rivaroxaban, darexaban, edoxaban), direct thrombin inhibitors (dabigatran) and PAR-1 antagonists (vorapaxar, atopaxar).

In another preferred embodiment the anticoagulant and oral anticoagulant, in particular apixaban, rivaroxaban, darexaban, edoxaban, dabigatran, vorapaxar, or atopaxar.

Thus, the subject to be tested may be on therapy with an oral anticoagulant or a vitamin K antagonist at the time of the testing (i.e. at the time at which the sample is received.

In a preferred embodiment, the method for predicting the risk of stroke in a subject further comprises i) the step of recommending anticoagulation therapy, or ii) of recommending an intensification of anticoagulation therapy, if the subject has been identified to be at risk to suffer from stroke. In a preferred embodiment, the method for predicting the risk of stroke in a subject further comprises i) the step of initiating anticoagulation therapy, or ii) of intensifying anticoagulation therapy, if the subject has been identified to be at risk to suffer from stroke (by the method of the present invention).

The term "recommending" as used herein means establishing a proposal for a therapy which could be applied to the subject. However, it is to be understood that applying the actual therapy whatsoever is not comprised by the term. The therapy to be recommended depends on the outcome of the provided by the method of the present invention.

In particular, the following applies:

If the subject to be tested does not receive anticoagulation therapy, the initiation of anticoagulation is recommended, if the subject has been identified to be at risk to suffer from stroke. Thus, anticoagulation therapy shall be initiated.

If the subject to be tested already receives anticoagulation therapy, the intensification of anticoagulation is recommended, if the subject has been identified to be at risk to suffer from stroke. Thus, anticoagulation therapy shall be intensified.

In a preferred embodiment, anticoagulation therapy is intensified by increasing the dosage of the anticoagulant, i.e. the dosage of the currently administered coagulant.

In a particularly preferred embodiment, anticoagulation therapy is intensified by increasing the replacing the currently administered anticoagulant with a more effective anticoagulant. Thus, a replacement of the anticoagulant is recommended.

It has been described that better prevention in high-risk patients is achieved with the oral anticoagulant apixaban versus the vitamin K antagonist warfarin as shown in Hijazi at al., 2016, FIG. 4.

Thus, it is envisaged that the subject to be tested is a subject who is treated with a vitamin K antagonist such as warfarin or dicumarol. If the subject has been identified to be at risk to suffer from stroke (by the method of the present invention, it the replacement of the vitamin K antagonist with an oral anticoagulant, in particular dabigatran, rivaroxaban or apixaban is recommended. According the therapy with the vitamin K antagonist is discontinued and therapy with an oral anticoagulant is initiated.

In a preferred embodiment of the present invention, the subject has a history of stroke or TIA (transient ischemic attack). In particular, the subject has a history of stroke.

Accordingly, it is envisaged that the subject has suffered from stroke or TIA prior to carrying out the method of the present invention (or to be more precise prior to obtaining the sample to be tested). Although the subject shall have suffered from stroke or TIA in the past, the subject shall not suffer from stroke and TIA at the time at which the sample to be tested is obtained).

As set forth above, the biomarkers Ang-2 and IGFBP7 could be increased in various diseases and disorders other than atrial fibrillation. In an embodiment of the present invention, it is envisaged that the subject does not suffer from such diseases and disorders.

The method of the present invention can be also used for the screening of larger populations of subjects. Therefore, it is envisaged, that at least 100 subjects, in particular at least 1000 subjects are assessed with respect to the risk of stroke Thus, the amount of the biomarker is determined in samples from at least 100, or in particular of from at least 1000 subjects. Moreover, it is envisaged that at least 10.000 subjects are assessed.

The term "sample" refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissue- or organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the biomarker(s) in the sample.

In a preferred embodiment of the present invention, the sample is a blood (i.e. whole blood), serum or plasma sample. Serum is the liquid fraction of whole blood that is obtained after the blood is allowed to clot. For obtaining the serum, the clot is removed by centrifugation and the supernatant is collected. Plasma is the acellular fluid portion of blood. For obtaining a plasma sample, whole blood is collected in anticoagulant-treated tubes (e.g. citrate-treated or EDTA-treated tubes). Cells are removed from the sample by centrifugation and the supernatant (i.e. the plasma sample) is obtained.

Preferably, the term "predicting the risk" as used herein refers to assessing the probability according to which the subject will suffer of stroke. Typically, it is predicted whether a subject is at risk (and thus at elevated risk) or not at risk (and thus at reduced risk) of suffering from stroke. Accordingly, the method of the present invention allows for differentiating between a subject who is at risk of stroke and a subject who is not at risk of stroke. Further, it is envisaged that the method of the present invention allows for differentiating between a reduced, average, and elevated risk of stroke.

As set forth above, the risk (and probability) of suffering from stroke within a certain time window shall be predicted. In accordance with the present invention, it is envisaged that the short-term risk or the long risk is predicted. E.g., the risk to suffer from stroke within one week or within one month is predicted. The shortest timespan observed in the studies underlying the present invention was 11 days. The subject had increased levels of Ang-2 (14.57 ng/ml) and IGFB7 (318 ng/ml). This indicates that not only a long term but also a short-term prediction is possible.

In an embodiment of the present invention, the predictive window is a period of about at least three months, about at least six months, or about at least one year. In another preferred embodiment, the predictive window is a period of about five years. Further, the predictive window might be a period of about six years (e.g. for the prediction of stroke).

In an embodiment, the predictive window is a period of up to 10 years. Thus, the risk to suffer from stroke within ten years is predicted.

In another embodiment, the predictive window is a period of up to 7 years. Thus, the risk to suffer from stroke within seven years is predicted.

In another embodiment, the predictive window is a period of up to 3 years. Thus, the risk to suffer from stroke within three years is predicted.

Also, it is envisaged that the predictive window a period of 1 to 10 years.

Preferably, the predictive window is calculated from the completion of the method of the present invention. More preferably, said predictive window is calculated from the time point at which the sample to be tested has been obtained.

As set forth above, the expression "predicting the risk of stroke" means that the subject to be analyzed by the method of the present invention is allocated either into the group of subjects being at risk of suffering from stroke, or into the group of subjects not being at risk of suffering from stroke. Thus, it is predicted whether the subject is at risk or not at risk of suffering from stroke. As used herein "a subject who is at risk of suffering from stroke", preferably, has an elevated risk of suffering from stroke (preferably within the predictive window). Preferably, said risk is elevated as compared to the average risk in a cohort of subjects. As used herein, "a subject who is not at risk of suffering from stroke", preferably, has a reduced risk of suffering from stroke (preferably within the predictive window). Preferably, said risk is reduced as compared to the average risk in a cohort of subjects. A subject who is at risk of suffering from stroke preferably has a risk of suffering from stroke of at least 7% or more preferably of at least 10%, preferably, within a predictive window of five years. A subject who is not at risk of suffering from stroke preferably has a risk of lower than 5%, more preferably of lower than 3% of suffering from stroke, preferably within a predictive window of five years.

The biomarker Angiopoietin-2 (abbreviated "Ang-2", frequently also referred to as ANGPT2) is well known in the art. It is a naturally occurring antagonist for both Ang-1 and TIE2 (see e.g. Maisonpierre et al., Science 277 (1997) 55-60). The protein can induce tyrosine phosphorylation of TEK/TIE2 in the absence of ANG-1. In the absence of angiogenic inducers, such as VEGF, ANG2-mediated loosening of cell-matrix contacts may induce endothelial cell apoptosis with consequent vascular regression. In concert with VEGF, it may facilitate endothelial cell migration and proliferation, thus serving as a permissive angiogenic signal. The sequence of human Angiopoietin is well known in the art. Uniprot lists three isoforms of Angiopoietin-2: Isoform 1 (Uniprot identifier: O15123-1), Isoform 2 (identifier: O15123-2) and Isoform 3 (O15123-3). In a preferred embodiment, the total amount of Angiopoietin-2 is determined. The total amount is preferably the sum of the amounts of complexed and free Angiopoietin-2.

IGFBP-7 (Insulin-like Growth Factor Binding Protein 7) is a 30-kDa modular glycoprotein known to be secreted by endothelial cells, vascular smooth muscle cells, fibroblasts, and epithelial cells (Ono, Y., et al., Biochem Biophys Res Comm 202 (1994) 1490-1496). Preferably, the term "IGFBP-7" refers to human IGFBP-7. The sequence of the protein is well known in the art and is e.g. accessible via UniProt (Q16270, IBP7 HUMAN), or via GenBank (NP_001240764.1). A detailed definition of the biomarker IGFBP-7 is e.g. provided in WO 2008/089994 which herewith is incorporated by reference in its entirety. There are two isoforms of IGFBP-7, Isoform 1 and 2 which are produced by alternative splicing. In an embodiment of the present invention, the total amount of both isoforms is measured (for the sequence, see the UniProt database entry (Q16270-1 and Q16270-2).

The term "determining" the amount of a biomarker as referred to herein (Ang-2 or IGFBP7, or of both biomarkers) refers to the quantification of the biomarker, e.g. to measuring the level of the biomarker in the sample, employing appropriate methods of detection described elsewhere herein. The terms "measuring" and "determining" are used herein interchangeably.

In an embodiment, the amount of a biomarker is determined by contacting the sample with an agent that specifically binds to the biomarker, thereby forming a complex between the agent and said biomarker, detecting the amount of complex formed, and thereby measuring the amount of said biomarker.

The biomarkers as referred to herein (such as Ang-2) can be detected using methods generally known in the art. Methods of detection generally encompass methods to quantify the amount of a biomarker in the sample (quantitative method). It is generally known to the skilled artisan which of the following methods are suitable for qualitative and/or for quantitative detection of a biomarker. Samples can be conveniently assayed for, e.g., proteins using Westerns and immunoassays, like ELISAs, RIAs, fluorescence- and luminescence-based immunoassays and proximity extension assays, which are commercially available. Further suitable methods to detect biomarkers include measuring a physical or chemical property specific for the peptide or polypeptide such as its precise molecular mass or NMR spectrum. Said methods comprise, e.g., biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

For the detection of biomarker proteins as referred to herein a wide range of immunoassay techniques using such an assay format are available, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled antibody to a target biomarker.

Methods employing electrochemiluminescent labels are well-known. Such methods make use of the ability of special metal complexes to achieve, by means of oxidation, an excited state from which they decay to ground state, emitting electrochemiluminescence. For review see Richter, M. M., Chem. Rev. 2004; 104: 3003-3036.

In an embodiment, the detection antibody (or an antigen-binding fragment thereof) to be used for measuring the amount of a biomarker is ruthenylated or iridinylated. Accordingly, the antibody (or an antigen-binding fragment thereof) shall comprise a ruthenium label. In an embodiment, said ruthenium label is a bipyridine-ruthenium(II) complex. Or the antibody (or an antigen-binding fragment thereof) shall comprise an iridium label. In an embodiment, said iridium label is a complex as disclosed in WO 2012/107419.

In an embodiment of the sandwich assay for the determination of Ang-2, the assay comprises a biotinylated first monoclonal antibody that specifically binds Ang-2 (as capture antibody) and a ruthenylated F(ab')2-fragment of a second monoclonal antibody that specifically binds Ang-2 as detection antibody). The two antibodies form sandwich immunoassay complexes with Ang-2 in the sample.

In an embodiment of the sandwich assay for the determination of IGFBP7, the assay comprises a biotinylated first monoclonal antibody that specifically binds IGFBP7 (as capture antibody) and a ruthenylated F(ab')2-fragment of a second monoclonal antibody that specifically binds IGFBP7 as detection antibody). The two antibodies form sandwich immunoassay complexes with IGFBP7 in the sample.

Measuring the amount of a polypeptide (such as Ang-2 or IGFBP7) may, preferably, comprise the steps of (a) contacting the polypeptide with an agent that specifically binds said polypeptide, (b) (optionally) removing non-bound agent, (c) measuring the amount of bound binding agent, i.e. the complex of the agent formed in step (a). According to a preferred embodiment, said steps of contacting, removing and measuring may be performed by an analyzer unit. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The agent which specifically binds the biomarker (herein also referred to as "binding agent") may be coupled covalently or non-covalently to a label allowing detection and measurement of the bound agent. Labeling may be done by direct or indirect methods. Direct labeling involves coupling of the label directly (covalently or non-covalently) to the binding agent. Indirect labeling involves binding (covalently or non-covalently) of a secondary binding agent to the first binding agent. The secondary binding agent should specifically bind to the first binding agent. Said secondary binding agent may be coupled with a suitable label and/or be the target (receptor) of a tertiary binding agent binding to the secondary binding agent. Suitable secondary and higher order binding agents may include antibodies, secondary antibodies, and the well-known streptavidin-biotin system (Vector Laboratories, Inc.). The binding agent or substrate may also be "tagged" with one or more tags as known in the art. Such tags may then be targets for higher order binding agents. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium complexes, iridium complexes, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, avail-able as ready-made stock solution from Roche Diagnostics), CDP-Star™ (Amersham Bio-sciences), ECF™ (Amersham Biosciences). A suitable enzyme-substrate combination may result in a colored reaction product, fluorescence or chemoluminescence, which can be determined according to methods known in the art (e.g. using a light-sensitive film or a suit-able camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also, the use of quantum dots as fluorescent labels is contemplated. A radioactive label can be detected by any method known and appropriate, e.g. a light-sensitive film or a phosphor imager.

The amount of a polypeptide may be, also preferably, determined as follows: (a) contacting a solid support comprising a binding agent for the polypeptide as described elsewhere herein with a sample comprising the peptide or polypeptide and (b) measuring the amount of peptide or polypeptide which is bound to the support. Materials for manufacturing supports are well-known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc.

In yet an aspect the sample is removed from the complex formed between the binding agent and the at least one marker prior to the measurement of the amount of formed complex. Accordingly, in an aspect, the binding agent may be immobilized on a solid support. In yet an aspect, the sample can be removed from the formed complex on the solid support by applying a washing solution.

"Sandwich assays" are among the most useful and commonly used assays encompassing a number of variations of the sandwich assay technique. Briefly, in a typical assay, an unlabeled (capture) binding agent is immobilized or can be immobilized on a solid substrate, and the sample to be tested is brought into contact with the capture binding agent. After a suitable period of incubation, for a period of time sufficient to allow formation of a binding agent-biomarker complex, a second (detection) binding agent labeled with a reporter molecule capable of producing a detectable signal is then added and incubated, allowing time sufficient for the formation of another complex of binding agent-biomarker-labeled binding agent. Any unreacted material may be washed away, and the presence of the biomarker is determined by observation of a signal produced by the reporter molecule bound to the detection binding agent. The results may either be qualitative, by simple observation of a visible signal, or may be quantitated by comparison with a control sample containing known amounts of biomarker.

The incubation steps of a typical sandwich assays can be varied as required and appropriate. Such variations include for example simultaneous incubations, in which two or more of binding agent and biomarker are co-incubated. For example, both, the sample to be analyzed and a labeled binding agent are added simultaneously to an immobilized capture binding agent. It is also possible to first incubate the sample to be analyzed and a labeled binding agent and to thereafter add an antibody bound to a solid phase or capable of binding to a solid phase.

The formed complex between a specific binding agent and the biomarker shall be proportional to the amount of the biomarker present in the sample. It will be understood that the specificity and/or sensitivity of the binding agent to be applied defines the degree of proportion of at least one marker comprised in the sample which is capable of being specifically bound. Further details on how the measurement can be carried out are also found elsewhere herein. The amount of formed complex shall be transformed into an amount of the biomarker reflecting the amount indeed present in the sample.

The terms "binding agent", "specific binding agent", "analyte-specific binding agent", "detection agent" and "agent that specifically binds to a biomarker" are used interchangeably herein. Preferably it relates to an agent that comprises a binding moiety which specifically binds the corresponding biomarker. Examples of "binding agents", "detection agents", "agents" are a nucleic acid probe, nucleic acid primer, DNA molecule, RNA molecule, aptamer, antibody, antibody fragment, peptide, peptide nucleic acid (PNA) or chemical compound. A preferred agent is an antibody which specifically binds to the biomarker to be determined. The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity (i.e. antigen-binding fragments thereof). Preferably, the antibody is a polyclonal antibody (or an antigen-binding fragment therefrom). More preferably, the antibody is a monoclonal antibody (or an antigen binding fragment therefore. Moreover, as described elsewhere herein, it is envisaged that two monoclonal antibodies are used that bind at different positions of Ang-2 (in a sandwich immunoassay). Thus, at least one antibody is used for the determination of the amount of Ang-2.

The term "specific binding" or "specifically bind" refers to a binding reaction wherein binding pair molecules exhibit a binding to each other under conditions where they do not significantly bind to other molecules. The term "specific binding" or "specifically binds", when referring to a protein or peptide as biomarker, preferably refers to a binding reaction wherein a binding agent binds to the corresponding biomarker with an affinity ("association constant" $K_a$) of at least $10^7$ $M^{-1}$. The term "specific binding" or "specifically binds" preferably refers to an affinity of at least $10^8$ $M^{-1}$ or even more preferred of at least $10^9$ $M^{-1}$ for its target molecule. The term "specific" or "specifically" is used to indicate that other molecules present in the sample do not significantly bind to the binding agent specific for the target molecule.

The term "amount" as used herein encompasses the absolute amount of a biomarker as referred to herein (such as Ang-2 or IGFBP7), the relative amount or concentration of the said biomarker as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response amounts determined from biological read out systems in response to the peptides or intensity signals obtained from specifically bound ligands. It is to be understood that values correlating to the aforementioned amounts or parameters can also be obtained by all standard mathematical operations.

The term "comparing" as used herein refers to comparing the amount of the biomarker (Ang-2 or IGFBP7) in the sample from the subject with the reference amount of the biomarker specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer-assisted. Thus, the comparison may be carried out by a computing device. The value of the determined or detected amount of the biomarker in the sample from the subject and the reference amount can be, e.g., compared to each other and the said comparison can be automatically carried out by a computer program executing an algorithm for the comparison. The computer program carrying out the said evaluation will provide the desired assessment in a suitable output format. For a computer-assisted comparison, the value of the determined amount may be compared to values corresponding to suitable references which are stored in a database by a computer program. The computer program may further evaluate the result of the comparison, i.e. automatically provide the desired assessment in a suitable output format. For a computer-assisted comparison, the value of the determined amount may be compared to values corresponding to suitable references which are stored in a database by a computer program. The computer program may further evaluate the result of the comparison, i.e. automatically provides the desired prediction in a suitable output format.

In accordance with the present invention, the amount of the biomarker as referred to herein, i.e. of Ang-2 and/or IGFBP7 shall be compared to a reference, i.e. to a reference amount (or to reference amounts). Accordingly, the reference is preferably a reference amount. The term "reference amount" is well understood by the skilled person. It is to be understood that the reference amount shall allow for the prediction of stroke or for the optimization of the clinical prediction rule for stroke as described herein elsewhere. E.g., in connection with the method for predicting the risk of stroke, the reference amount preferably refers to an amount which allows for allocation of a subject into either (i) the group of subjects suffering from atrial fibrillation or (ii) the group of subjects not suffering from atrial fibrillation. A suitable reference amount may be determined from a reference sample to be analyzed together, i.e. simultaneously or subsequently, with the test sample.

It is to be understood that the amount of Ang-2 is compared to a reference amount for Ang-2 and/or the amount of IGFBP7 is compared to a reference amount of the IGFBP7. If the amounts of two markers are determined, it is also envisaged that a combined score is calculated based on the amounts of Ang-2 and IGFBP7. In a subsequent step, the score is compared to a reference score.

Reference amounts can, in principle, be calculated for a cohort of subjects as specified above based on the average or mean values for a given biomarker by applying standard methods of statistics. In particular, accuracy of a test such as a method aiming to diagnose an event, or not, is best described by its receiver-operating characteristics (ROC) (see especially Zweig M H. et al., Clin. Chem. 1993; 39:561-577). The ROC graph is a plot of all the sensitivity versus specificity pairs resulting from continuously varying the decision threshold over the entire range of data observed. The clinical performance of a diagnostic method depends on its accuracy, i.e. its ability to correctly allocate subjects to a certain prognosis or diagnosis. The ROC plot indicates the overlap between the two distributions by plotting the sensitivity versus 1—specificity for the complete range of thresholds suitable for making a distinction. On the y-axis is sensitivity, or the true-positive fraction, which is defined as the ratio of number of true-positive test results to the product of number of true-positive and number of false-negative test results. It is calculated solely from the affected subgroup. On the x-axis is the false-positive fraction, or 1—specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/1—specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa.

Qualitatively, the closer the plot is to the upper left corner, the higher the overall accuracy of the test. Dependent on a desired confidence interval, a threshold can be derived from the ROC curve allowing for the diagnosis for a given event with a proper balance of sensitivity and specificity, respectively. Accordingly, the reference to be used for the method of the present invention, i.e. a threshold which allows to assess atrial fibrillation can be generated, preferably, by establishing a ROC for said cohort as described above and deriving a threshold amount therefrom. Dependent on a desired sensitivity and specificity for a diagnostic method, the ROC plot allows deriving a suitable threshold. It will be understood that an optimal sensitivity is desired for e.g. excluding a subject being at risk of stroke (i.e. a rule out) whereas an optimal specificity is envisaged for a subject to be predicted to be at risk of stroke (i.e. a rule in).

Preferably, the term "reference amount" herein refers to a predetermined value. Said predetermined value shall allow for predicting the risk of stroke.

Preferably, the reference amount, i.e. the reference amount shall allow for differentiating between a subject who is at risk of suffering from stroke and a subject who is not at risk of suffering from stroke.

The diagnostic algorithm is preferably as follows:

Preferably, an amount of Ang-2 and/or an amount of IGFBP7 which is increased as compared to the reference amount is indicative for a subject who is at risk to suffer from stroke, and/or an amount of Ang-2 and/or an amount of IGFBP7 which is decreased (or not altered) as compared to the reference amount is indicative for a subject who is at not at risk to suffer from stroke.

Preferred reference amounts are given in the Examples section. E.g. with respect to Ang-2, the reference amount may be 2.4 ng/ml, and with respect to IGFBP7 178 pg/ml, preferably in a blood, serum or plasma sample. However, it will be understood by the skilled person that depending on the desired sensitivity and specificity other reference amounts would also allow for a reliable prediction.

In the studies underlying the present invention, it has been further shown that the determination of Ang-2 and/or IGFBP7 allows for improving the prediction accuracy of a clinical stroke risk score for a subject. Thus, the combined determination of clinical stroke risk score and the determination of Ang-2 and/or IGFBP7 allows for an even more reliable prediction of stroke as compared to the determination of Ang-2 and/or IGFBP7 or the determination of the clinical stroke risk score alone.

Accordingly, the method for predicting the risk of stroke may further comprise the combination of the amount of Ang-2 and/or IGFBP7 with the clinical stroke risk score. Based on the combination of the amount of Ang-2 and/or IGFBP7 and the clinical risk score, the risk of stroke of the test subject is predicted.

Accordingly, the present invention in particular relates to a method for predicting the risk of stroke in a subject, comprising the steps of a) determining the amount of Ang-2 and/or the amount of Insulin-like growth factor-binding protein 7 (IGFBP7) in a sample from the subject having a known clinical stroke risk score, b) assessing the clinical stroke risk score for said subject, and c) predicting the risk of stroke based on the results of steps a) and b).

In accordance with the method of the present invention, it is envisaged that the subject is a subject who has a known clinical stroke risk score. Accordingly, the value for the clinical stroke risk score is known for the subject.

Alternatively, the method may comprise obtaining or providing the value for the clinical stroke risk score. Accordingly, step b) preferably comprises providing the value for the clinical risk score. Preferably, the value is a number. In an embodiment, the clinical stroke risk score is generated by one of the clinically based tools available to physicians. Preferably, the value provided by determining the value for the clinical stroke risk score for the subject. More preferably, the value for the subject is obtained from patient record databases and medical history of the subject. The value for the score therefore can be also determined using historical or published data of the subject.

In accordance with the present invention, the amount of Ang-2 and/or IGFBP7 is combined with the clinical stroke risk score. This means preferably that a value for the amount of Ang-2 and/or IGFBP7 is combined with the clinical stroke risk score. Accordingly, the values are operatively combined to predict the risk of the subject to suffer from stroke. By combining the value, a single value may be calculated, which itself can be used for the prediction.

Clinical stroke risk scores are well known in the art. E.g. said scores are described in Kirchhof P. et al., (European Heart Journal 2016; 37: 2893-2962). In an embodiment, the score is $CHA_2DS_2$-VASc-Score. In another embodiment, the score is the $CHADS_2$ Score. (Gage B F. Et al., JAMA, 285 (22) (2001), pp. 2864-2870) and ABC score, i.e. the ABC (age, biomarkers, clinical history) stroke risk score (Hijazi Z. et al., Lancet 2016; 387(10035): 2302-2311). All publications in this paragraph are herewith incorporated by reference with respect to their entire disclosure content.

Thus, in an embodiment of the present invention, the clinical stroke risk score is the CHA2DS2-VASc-Score.

In another embodiment of the present invention, the clinical stroke risk score is the CHADS2 Score.

In a further embodiment, the clinical risk score is the ABC Score. The ABC stroke risk score is a novel biomarker-based risk score for predicting stroke in AF was validated in a large cohort of patients with AF and further externally validated in an independent AF cohort (see Hijazi et al., 2016). It includes the age of the subject, the blood, serum or plasma levels of cardiac Troponin T and NT-proBNP in said subject, and information on whether the subject has a history of stroke. Preferably, the ABC stroke score is the score as disclosed in Hijazi et al.

In a preferred embodiment, the above method for predicting the risk of stroke in a subject further comprises the step of recommending anticoagulation therapy or of recommending an intensification of anticoagulation therapy if the subject has been identified to be at risk to suffer from stroke (as described elsewhere herein).

Method for Improving the Prediction Accuracy of a Clinical Stroke Risk Score

The present invention further relates to a method for improving the prediction accuracy of a clinical stroke risk score for a subject, comprising the steps of
a) determining the amount of Ang-2 and/or IGFBP7 in a sample from a subject as specified elsewhere herein, and
b) combining the amount (in particular, a value for the amount) of Ang-2 and/or IGFBP7 with the clinical stroke risk score, whereby the prediction accuracy of said clinical stroke risk score is improved.

The method may comprise the further step of c) improving prediction accuracy of said clinical stroke risk score based on the results of step b).

The definitions and explanations given herein above in connection with the method of assessing atrial fibrillation, in particular of predicting the risk of an adverse event (such as stroke) preferably apply to the aforementioned method as well E.g., it envisaged that the subject is a subject who has a known clinical stroke risk score. Alternatively, the method may comprise obtaining or providing the value for the clinical stroke risk score.

In accordance with the present invention, the amount of Ang-2 and/or IGFBP7 is combined with the clinical stroke risk score. This means preferably, that the value for the amount of Ang-2 and/or IGFBP7 is combined with the clinical stroke risk score. Accordingly, the values are operatively combined to improve the prediction accuracy of said clinical stroke risk score.

The present invention further concerns a method of aiding in the prediction of the risk of stroke of a subject, said method comprising the steps of:
a) obtaining a sample from a subject as referred to herein in connection with the method of the present invention,
b) determining the amount of the biomarker Ang-2 and/or IGFBP7 in said sample, and
c) providing information on the determined amount of the biomarker Ang-2 and/or IGFBP7 to the attending physician of the subject, thereby aiding in the prediction of the risk The attending physician shall be the physician who requested the determination of the biomarker(s). The aforementioned method shall aid the attending physician in the assessment of atrial fibrillation. Thus, the method does not encompass the actual prediction of the risk.

Step a) of the aforementioned method of obtaining the sample does not encompass the drawing of the sample from the subject. Preferably, the sample is obtained by receiving a sample from said subject. Thus, the sample can have been delivered.

The present invention further relates to a method, comprising:
a) providing a test for the biomarker Ang-2 and/or IGFBP7, and
b) providing instructions for using of test results obtained or obtainable by said test(s) in the assessment of atrial fibrillation.

The purpose of the aforementioned method is, preferably, the aid in the prediction of the risk of stroke as described elsewhere herein in more detail.

The instructions shall contain a protocol for carrying out the method of assessing atrial fibrillation as described herein above. Further, the instructions shall contain at least one value for a reference amount for Ang-2 and/or IGFBP7.

The "test" is preferably a kit adapted to carry out the method of assessing atrial fibrillation. The term "Kit" is explained herein below. E.g., said kit shall comprise at least one detection agent for the biomarker Ang-2 and/or at least one detection agent for the biomarker IGFBP7. The detection agents for the two biomarkers can be provided in a single kit or in two separate kits.

The test result obtained or obtainable by said test, is the value for the amount of the biomarker(s).

In an embodiment, step b) comprises providing instructions for using of test results obtained or obtainable by said test(s) in prediction of stroke (as described herein elsewhere).

The definitions and explanations given herein above, preferably, apply mutatis mutandis to the following:

The present invention further relates to the use of
i) the biomarker Ang-2 and/or the biomarker IGFBP7, and/or
ii) at least one detection agent that specifically binds to Ang-2 and/or at least one detection agent that specifically binds to IGFBP7 in a sample from a subject for predicting the risk of stroke of said subject.

Further, the present invention contemplates the use of
i) the biomarker Ang-2 and/or the biomarker IGFBP7, and/or
ii) at least one detection agent that specifically binds to Ang-2 and/or at least one detection agent that specifically binds to IGFBP7 in a sample from a subject for improving the prediction accuracy of a clinical stroke risk score.

Finally, the present invention relates to the use of
i) the biomarker Ang-2 and/or the biomarker IGFBP7, and/or
ii) at least one detection agent that specifically binds to Ang-2 and/or at least one detection agent that specifically binds to IGFBP7,
in a sample from a subject,
in combination with a clinical stroke risk score,
for predicting the risk of a subject to suffer from stroke.

The terms mentioned in connection with the aforementioned use such as "sample", "subject", "detection agent", "Ang-2", "IGFBP7", "specifically binding", "stroke", and "prediction the risk" have been defined in connection with the methods of the present invention. The definitions and explanations apply accordingly.

Preferably, the aforementioned uses are in vitro uses. Moreover, the detection agent is, preferably, an antibody such as a monoclonal antibody (or an antigen binding fragment thereof) which specifically binds to the biomarker.

All references cited in this specification are herewith incorporated by reference with respect to their entire disclosure content and the disclosure content specifically mentioned in this specification.

EXAMPLES

The invention will be merely illustrated by the following Examples. The said Examples shall, whatsoever, not be construed in a manner limiting the scope of the invention.

Example 1

The ability of circulating IGFBP-7 and of circulating Ang-2 to predict the risk for the occurrence of stroke was assessed in a prospective, multicentric registry of patients with documented atrial fibrillation (Conen D., Forum Med Suisse 2012; 12:860-862; Blum S. (J Am Heart Assoc. 2017; 6:e005401. DOI: 10.1161/JAHA.116.005401).

The Beat AF cohort comprises baseline plasma samples of 1553 patients that were followed for 7-years. Mean age was 70+/−11 years among women and 67+/−12 years among men. The primary endpoint was stroke or systemic embolism. 70 patients experienced a stroke within the follow up period, most of them within 3 years. Between 2010 and 2014, 1553 patients with documented AF were enrolled across 7 centers in Switzerland. At that time, therapy was just changed from vitamin K antagonists to oral anticoagulation with about 70% of the enrolled patients receiving oral anticoagulation and with a proportion of the patients receiving vitamin antagonists still at the time of blood sampling. The majority of patients in the Beat AF cohort already received "new treatments, novel oral anticoagulants" (NOAC, OAC) instead of Vitamin K antagonists for thromboprophylaxis and stroke prevention.

NOAC comprise direct factor Xa inhibitors (apixaban, rivaroxaban, darexaban, edoxaban), direct thrombin inhibitors (dabigatran) and PAR-1 antagonists (vorapaxar, atopaxar). Vitamin K antagonists comprise warfarin and dicumarol. All patients were required to have AF that was previously documented by ECG, rhythm strip, or device interrogation. About 60% of the enrolled patients had paroxysmal AF, 20% persistent AF and 20% permanent AF. Paroxysmal AF was assessed by clinical diagnosis including self-limiting AF with patients presenting in sinus rhythm at the time of blood sampling as well as patients with several episodes of AF and ongoing AF at the time of sampling. Exclusion criteria were the inability to sign informed consent and the exclusive presence of short transient episodes of AF (eg, AF after cardiac surgery).

IGFBP-7 levels were available for 69 patients with stroke outcome and for 1435 patients without stroke. Angiopoetin-2 levels were available for 69 patients with stroke outcome and for 1430 patients without stroke.

In order to quantify the univariate prognostic value of IGFBP-7 and of Ang-2 proportional hazard models were used with the outcome stroke.

The univariate prognostic performance of IGFBP-7 or Ang-2 was assessed by two different incorporations of the prognostic information given by IGFBP-7 or by Ang-2 respectively. The first proportional hazard model included IGFBP-7 or Ang-2 binarized at the median (178 pg/mL or 2.4 ng/ml respectively) and therefore comparing the risk of patients with IGFBP-7 or Ang-2 below or equal to the median versus patient with IGFBP-7 or Ang-2 above the median.

The second proportional hazard model included the original IGFBP-7 or Ang-2 levels but transformed to a log 2 scale. The log 2 transformation was performed in order to enable a better model calibration.

The association between the risk for experiencing a stroke with the baseline value of IGFBP-7 or Ang-2 is highly significant in both models.

The hazard ratio for the binarized IGFBP-7 implies a 3.14-fold higher risk for a stroke in the patient group with baseline IGFBP-7 >178 pg/mL versus the patient group with baseline IGFBP-7<=178 pg/mL.

The results of the proportional hazard model including IGFBP-7 as log 2 transformed linear risk predictor suggest the log 2 transformed values IGFBP-7 are proportional to the risk for experiencing a stroke. The hazard ratio of 3.09 can be interpreted in a way that a 2-fold increase of IGFBP-7 is associated with 3.09 increase of risk for a stroke.

The hazard ratio for the binarized Angiopoetin-2 implies a 3.31-fold higher risk for a stroke in the patient group with baseline Angiopoetin-2 >2.4 ng/ml versus the patient group with baseline Angiopoetin-2<=2.4 ng/ml.

The results of the proportional hazard model including Angiopoetin-2 as log 2 transformed linear risk predictor suggest the log 2 transformed values Angiopoetin-2 are proportional to the risk for experiencing a stroke. The hazard ratio of 1.78 can be interpreted in a way that a 2-fold increase of Angiopoetin-2 is associated with 1.78 increase of risk for a stroke.

The absolute survival rates in the two groups based on the dichotomized baseline IGFBP-7 or Ang-2 measurement (<=178 pg/mL vs >178 pg/mL; <=2.4 ng/ml vs >2.4 ng/ml respectively) are illustrated by a Kaplan-Meier plot.

In order to assess if the prognostic value of IGFBP-7 or Ang-2 is independent from known clinical and demographic risk factors a weighted proportional cox model including in addition the variables age, sex, CHF history, history of hypertension, Stroke/TIA/Thromboembolism history, vascular disease history and diabetes history was calculated.

Figure 1A:
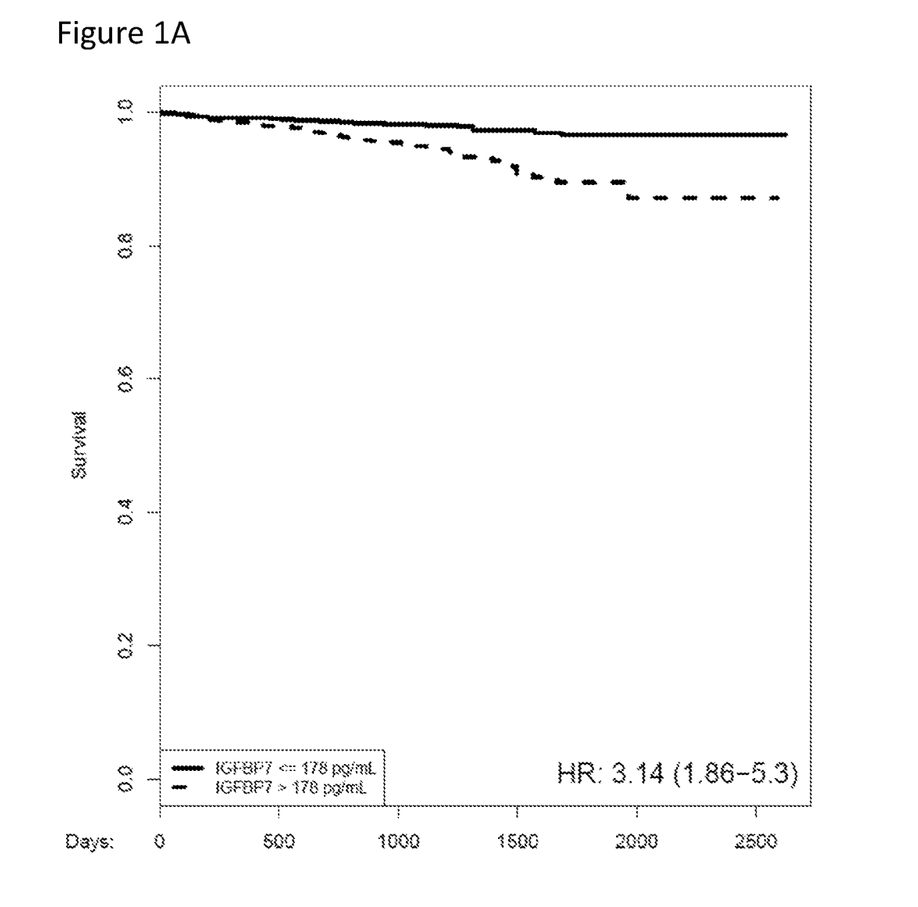
FIG. 1A: Weighted Kaplan-Meier survival estimates for the two groups defined by baseline IGFBP-7 measurement <=178 pg/mL vs >178 pg/mL.

FIG. 1A shows the weighted Kaplan-Meier curves for the two patient groups with baseline IGFBP-7 measurement <=178 pg/mL vs >178 pg/mL. As easily seen the risk for the two groups for the occurrence of a stroke differs significantly. As shown in FIG. 1 IGFBP-7 may help to identify patients at elevated risk of stroke, even in a population of patients with atrial fibrillation that receive oral anticoagulation or vitamin antagonists.

Figure 1B:
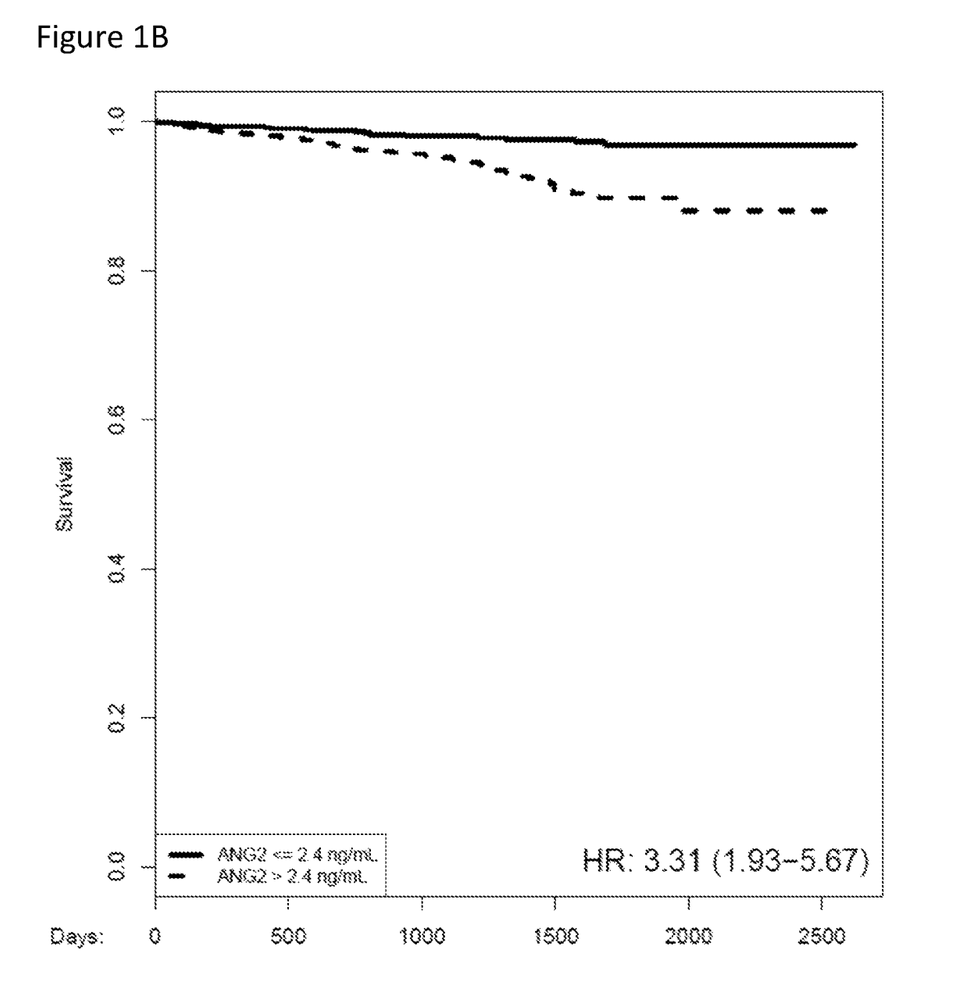
FIG. 1B: Weighted Kaplan-Meier survival estimates for the two groups defined by baseline Angiopoetin-2 measurement <=2.4 ng/ml vs >2.4 ng/ml.

FIG. 1B shows the weighted Kaplan-Meier curves for the two patient groups with baseline Angiopoetin-2 measurement <=2.4 ng/ml vs >2.4 ng/ml. As easily seen the risk for the two groups for the occurrence of a stroke differs significantly. As shown in FIG. 1B Ang-2 may help to identify

TABLE 1

Results result of the univariate weighted proportional hazard model including the binarized and log2 transformed IGFBP-7 and Ang-2.

| | Hazard Ratio (HR) | 95%-CI HR | P-Value | | Hazard Ratio (HR) | 95%-CI HR | P-Value |
|---|---|---|---|---|---|---|---|
| IGFBP-7 log2 | 3.090 | 1.838-5.193 | <0.001 | Angiopoetin-2 log2 | 1.779 | 1.356-2.333 | <0.001 |
| Baseline IGFBP-7 > 178 pg/mL vs IGFBP-7 <= 178 pg/mL | 3.137 | 1.857-5.300 | <0.001 | Baseline Angiopoetin-2 > 2.4 ng/ml vs Angiopoetin-2 <= 2.4 ng/ml | 3.309 | 1.931-5.671 | <0.001 |

Table 1 shows the results of the two univariate weighted proportional hazard models including the binarized or the log 2 transformed IGFBP-7 or Ang-2.

patients at elevated risk of stroke, even in a population of patients with atrial fibrillation that receive oral anticoagulation or vitamin antagonists.

TABLE 2

Multivariate proportional hazard model including IGFBP-7,
Ang-2 and relevant clinical and demographic variables.

| | Hazard Ratio (HR) | 95%-CI HR | P-Value | | Hazard Ratio (HR) | 95%-CI HR | P-Value |
|---|---|---|---|---|---|---|---|
| History hypertension | 1.0157 | 0.5696-1.8112 | 0.9579 | History hypertension | 0.9743 | 0.5473-1.7342 | 0.9294 |
| Age | 1.0428 | 1.0127-1.0738 | 0.0051 | Age | 1.0471 | 1.0189-1.0761 | 0.0010 |
| History Stroke/ TIA/embolism | 2.2011 | 1.3114-3.6944 | 0.0028 | History Stroke/ TIA/embolism | 2.1692 | 1.2927-3.6401 | 0.0034 |
| Sex = male | 0.7803 | 0.4725-1.2886 | 0.3323 | Sex = male | 0.8429 | 0.5108-1.3909 | 0.5036 |
| History CHF | 0.9266 | 0.5049-1.7005 | 0.8057 | History CHF | 0.8827 | 0.4839-1.6102 | 0.6841 |
| History vascular disease | 1.0464 | 0.5978-1.8317 | 0.8738 | History vascular disease | 1.054 | 0.6059-1.8333 | 0.8524 |
| IGFBP-7 (log2 transformed) | 1.9101 | 0.944-3.8648 | 0.0719 | Ang-2 (log2 transformed) | 1.5061 | 1.1006-2.0609 | 0.0105 |

Table 2 shows the results of a proportional hazard model including IGFBP-7 (log 2 transformed) in the combination with clinical and demographic variables. Although the point estimator of hazard ratio for IGFBP-7 is still notable above 1 the p-value is now above 0.05. However given the still high hazard ratio and that the c-index of the model including only the clinical variables shown in table 2 improves by 0.0054 with the addition of IGFBP-7 it can be expected that the effect of IGFBP-7 would significant on larger cohort with e.g. 140 events.

Table 2 shows the results of a proportional hazard model including Angiopoetin-2 (log 2 transformed) in the combination with clinical and demographic variables. It clearly shows that the prognostic effect of Angiopoetin-2 remains significant if adjusting for the prognostic effect of relevant clinical and demographic variables In order to assess the ability of IGFBP-7 or Ang-2 to improve existing risk scores for the prognosis of stroke weighted proportional hazard models including the $CHADS_2$ respectively the $CHA_2DS_2$-VASc score and IGFBP-7 or Ang-2 (log 2 transformed) were calculated.

TABLE 3

Weighted proportional hazard model combining the
$CHADS_2$ score with IGFBP-7 and Ang-2 (log2 transformed)

| | Hazard Ratio (HR) | 95%-CI HR | P-Value | | Hazard Ratio (HR) | 95%-CI HR | P-Value |
|---|---|---|---|---|---|---|---|
| CHADS2 score | 1.5023 | 1.2547-1.7988 | <0.001 | CHADS2 score | 1.5022 | 1.2592-1.7921 | <0.001 |
| IGFBP-7 (log2 transformed) | 1.9149 | 1.0353-3.5415 | 0.038 | Ang-2 (log2 transformed) | 1.4490 | 1.0776-1.9485 | 0.014 |

Table 3 shows the results of the weighted proportional hazard model combining the $CHADS_2$ score with IGFBP-7 and Ang-2 (log 2 transformed). Also in this model, IGFBP-7 and Ang-2 can add prognostic information to the $CHADS_2$ score.

TABLE 4

Weighted proportional hazard model combining the
$CHA_2DS_2$-VASc score with IGFBP-7 and Ang-2 (log2 transformed)

| | Hazard Ratio (HR) | 95%-CI HR | P-Value | | Hazard Ratio (HR) | 95%-CI HR | P-Value |
|---|---|---|---|---|---|---|---|
| CHA2DS2-VASc score | 1.3896 | 1.2051-1.6025 | <0.001 | CHA2DS2-VASc score | 1.3849 | 1.2040-1.5931 | <0.001 |
| IGFBP-7 (log2 transformed) | 1.7383 | 0.9251-3.2664 | 0.086 | Ang-2 (log2 transformed) | 1.3802 | 1.0201-1.8674 | 0.037 |

Table 4 shows the results of the weighted proportional hazard model combining the $CHA_2DS_2$-VASc score with IGFBP-7 and Ang-2 (log 2 transformed). Similar to Table 2 the hazard ratio of IGFP-7 is still above 1 but again with a p-value not reaching 0.05. Also, here the relative small number of events has to be considered. Also in this model, Angiopoetin-2 can add prognostic information to the $CHA_2DS_2$-VASc score.

The c-indices of the $CHADS_2$ and the $CHA_2DS_2$-VASc score were compared to the c-indices of these models.

TABLE 5

C-indexes of IGFBP-7, Ang-2 the $CHADS_2$, $CHA_2DS_2$-VASc and ABC score and their combination with IGFBP-7 or Ang-2.

|  | C-Index |  | C-Index |
|---|---|---|---|
| IGFBP-7 univariate | 0.6659 | Ang-2 univariate | 0.6253 |
| CHADS2 | 0.6706 | CHADS2 | 0.6706 |
| CHADS2 + IGFBP-7 | 0.6820 | CHADS2 + Ang-2 | 0.6833 |
| CHA2DS2-VASc | 0.6915 | CHA2DS2-VASc | 0.6915 |
| CHA2DS2-VASc + IGFBP-7 | 0.6956 | CHA2DS2-VASc + Ang-2 | 0.6982 |
| ABC score | 0.6804 | ABC score | 0.6804 |
| ABC score + IGFBP-7 | 0.6843 | ABC score + Ang-2 | 0.6831 |

The shortest time to stroke observed was 11 days after blood sampling from a 75 years old female patient with permanent atrial fibrillation without any history of stroke, TIA, vascular disease, hypertension or diabetes. At baseline elevated titers of IGFBP-7 (318 pg/mL) and of Ang-(14.6 ng/mL) were detected. The patient had permanent atrial fibrillation and received anticoagulants. The patient had no history of heart failure and no diagnosis of heart failure.

The median values of IGFBP-7 and of Ang-2 were compared in patients developing stroke with and without history of heart failure (HF).

TABLE 6

IGFBP-7 and Ang-2 in patients with and without a history of heart failure

| AF Type | Patients w/o HF developing stroke (n) | Time to stroke (days) | Ang-2 (ng/mL) | IGFBP-7 (pg/mL) |
|---|---|---|---|---|
| All | 54 | 683 | 2.6 | 187 |
|  | Patients w HF developing stroke |  |  |  |
| All | 16 | 889 | 4.2 | 216 |
|  | All patients |  |  |  |
| All | 70 | 705 | 3.5 | 205 |

As shown in Table 6 elevated levels of IGFBP-7 above 178 pg/mL and of Ang-2 above 2.4 ng/mL were observed in the patients developing stroke irrespective of a history of heart failure. Elevated levels of IGFBP-7 above 178 pg/mL and of Ang-2 above 2.4 ng/mL were also observed in the subset 54 patients without a diagnosis of heart failure and without a history of heart failure.

The results suggest that IGFBP-7 can be used in several ways to predict the risk for a future stroke for a new patient, either alone, or as a combination to considerably improve the clinical scores in predicting stroke risk (such as CHADS2, $CHA_2DS_2$-VASc and ABC). The patient may be a patient with atrial fibrillation and already receiving anticoagulation or vitamin Ka antagonists.

For a new patient IGFBP-7 could be measured and compared to a pre-defined cutoff (e.g. 178 pg/mL). If the measured value for the new patient is above the predefined cutoff the patient is considered to have a high risk for the experience of stroke and appropriate clinical measures could be initiated.

It is also possible to define more than two risk groups based on an increasing set of cutoffs. A patient would then be assigned to one of the risk groups based on the value of his IGFBP-7 measurement. The risk for a stroke is expected to increase over the different risk groups.

Alternatively, it would be also possible to transform the results of IGFBP-7 directly into a continuous risk score based on pre-defined suitable transformation function.

In addition, it is possible to use the value of IGFBP-7 in a combination with a risk score based on clinical and demographic variables (e.g. $CHA_2DS_2$-VASc score or ABC score) and thereby improve the precision of the risk prediction.

For a new patient the value for risk score would be assessed and combined in an appropriate way with the measured IGFBP-7 values (potentially log 2 transformed), e.g. by creating a weighted sum of the risk score results and the IGFBP-7 value with appropriate pre-defined weights (e.g. as shown in table 3).

The results suggest that Angiopoetin-2 can be used in several ways to predict the risk for a future stroke for a new patient, either alone, or as a combination to considerably improve the clinical scores in predicting stroke risk (such as CHADS2, $CHA_2DS_2$-VASc and ABC). The patient may be a patient with atrial fibrillation and already receiving anticoagulation or vitamin Ka antagonists.

For a new patient Angiopoetin-2 could be measured and compared to a pre-defined cutoff (e.g. 2.4 ng/ml). If the measured value for the new patient is above the predefined cutoff the patient is considered to have a high risk for the experience of stroke and appropriate clinical measures could be initiated.

It is also possible to define more than two risk groups based on an increasing set of cutoffs. A patient would then be assigned to one of the risk groups based on the value of his Angiopoetin-2 measurement. The risk for a stroke is expected to increase over the different risk groups.

Alternatively, it would be also possible to transform the results of Angiopoetin-2 directly into a continuous risk score based on pre-defined suitable transformation function.

In addition, it is possible to use the value of Angiopoetin-2 in a combination with a risk score based on clinical and demographic variables (e.g. $CHA_2DS_2$-VASc score or ABC score) and thereby improve the precision of the risk prediction.

For a new patient the value for risk score would be assessed and combined in an appropriate way with the measured Angiopoetin-2 values (potentially log 2 transformed), e.g. by creating a weighted sum of the risk score results and the Angiopoetin-2 value with appropriate pre-defined weights (e.g. as shown in table 3).

The invention claimed is:
1. A method for predicting the risk of stroke of a human subject currently receiving anticoagulation therapy, comprising the steps of
   (a) detecting complexes formed by binding of an agent that specifically binds Angiopoietin-2 (Ang-2) and measuring the amount of Angiopoietin-2 (Ang-2) and/or detecting complexes formed by binding of an agent that specifically binds Insulin-like Growth Factor Binding Protein 7 (IGFBP-7) and measuring the amount of Insulin-like growth factor-binding protein 7 (IGFBP7)

in a sample from a human subject who suffers from atrial fibrillation, wherein the sample is blood, serum or plasma, (b) comparing the amount of Ang-2 and/or the amount of IGFBP7 to a reference amount, whereby the risk of stroke is predicted, (c) identifying a subject as being at elevated risk of stroke when an amount of Ang-2 and/or an amount of IGFBP7 is increased as compared to the reference amount, wherein elevated risk is a risk that is elevated as compared to a subject who has a reduced amount of Ang-2 and/or IGFBP7 as compared to the reference amount, and (d) administering an intensification of anticoagulation therapy to the subject identified to be at elevated risk to suffer from stroke.

2. The method of claim 1, wherein the atrial fibrillation is paroxysmal, persistent or permanent atrial fibrillation.

3. The method of claim 1, wherein the subject has a history of stroke or TIA (transient ischemic attack).

4. The method of claim 1, wherein the predictive window is a period of up to 10 years.

5. The method of claim 1, wherein the anticoagulation therapy is selected from the group consisting of heparin, a coumarin derivative, dabigatran, rivaroxaban, apixaban, tissue factor pathway inhibitor (TFPI), antithrombin III, factor IXa inhibitors, factor Xa inhibitors, inhibitors of factors Va and VIIIa, thrombin inhibitors and combinations thereof.

6. The method of claim 1, wherein an analyzer unit is used to conduct an assay to detect complexes formed by binding of an agent that specifically binds Angiopoietin-2 (Ang-2) and to measure the amount of Angiopoietin-2 (Ang-2) and/or an analyzer unit is used to conduct an assay to detect complexes formed by binding of an agent that specifically binds Insulin-like Growth Factor Binding Protein 7 (IGFBP-7) to measure the amount of Insulin-like growth factor-binding protein 7 (IGFBP7) in a sample from the human subject who suffers from atrial fibrillation.

7. The method of claim 1, wherein the intensification of anticoagulation therapy is the replacement of a vitamin K antagonist with a new oral anticoagulant.

8. The method of claim 7, wherein the new oral anticoagulant is selected from the group consisting of apixaban, rivaroxaban, darexaban, edoxaban, dabigatran, vorapaxar, and atopaxar.

9. The method of claim 7, wherein the vitamin K antagonist is selected from the group consisting of warfarin and dicumarol.

10. The method of claim 1, wherein the intensification of anticoagulation therapy is an increase in dosage of the administered anticoagulant therapy.

11. The method of claim 1, wherein the elevated risk of stroke is a risk of at least 7% of suffering stroke within five years.

* * * * *